US012773374B2

(12) United States Patent
Fujimori et al.

(10) Patent No.: US 12,773,374 B2
(45) Date of Patent: Oct. 27, 2026

(54) DENTAL ADHESIVE COMPOSITION

(71) Applicant: GC Corporation, Shizuoka (JP)

(72) Inventors: Kensuke Fujimori, Tokyo (JP); Miki Yamashita, Tokyo (JP); Kosuke Honda, Tokyo (JP)

(73) Assignee: GC Corporation, Shizuoka (JP)

( * ) Notice: Subject to any disclaimer, the term of this patent is extended or adjusted under 35 U.S.C. 154(b) by 683 days.

(21) Appl. No.: 18/263,584

(22) PCT Filed: Dec. 7, 2021

(86) PCT No.: PCT/JP2021/044951
§ 371 (c)(1),
(2) Date: Jul. 31, 2023

(87) PCT Pub. No.: WO2022/168429
PCT Pub. Date: Aug. 11, 2022

(65) Prior Publication Data

US 2024/0108554 A1 Apr. 4, 2024

(30) Foreign Application Priority Data

Feb. 5, 2021 (JP) ................................ 2021-017790

(51) Int. Cl.
*A61K 6/30* (2020.01)

(52) U.S. Cl.
CPC .................................... *A61K 6/30* (2020.01)

(58) Field of Classification Search
CPC ...................................................... A61K 6/30
USPC ........................................................ 523/118
See application file for complete search history.

(56) References Cited

U.S. PATENT DOCUMENTS

| | | | | |
|---|---|---|---|---|
| 11,744,782 | B2 * | 9/2023 | Mitamura | A61K 6/887 514/770 |
| 2010/0048761 | A1 | 2/2010 | Ishino et al. | |
| 2010/0056665 | A1 | 3/2010 | Sekiguchi | |
| 2010/0311864 | A1 | 12/2010 | Arita et al. | |
| 2019/0000722 | A1 * | 1/2019 | Suzuki | A61K 6/62 |
| 2021/0169749 | A1 * | 6/2021 | Mitamura | A61K 6/836 |

FOREIGN PATENT DOCUMENTS

| | | | | |
|---|---|---|---|---|
| JP | 2000-016911 | | 1/2000 | |
| JP | 2010-280630 | | 12/2010 | |
| JP | 2017-200881 | | 11/2017 | |
| WO | 2008/087978 | | 7/2008 | |
| WO | 2008/114621 | | 9/2008 | |
| WO | WO-2019031488 | A1 * | 2/2019 | A61K 6/61 |
| WO | WO-2020111142 | A1 * | 6/2020 | A61K 6/79 |

OTHER PUBLICATIONS

International Search Report for PCT/JP2021/044951 mailed on Feb. 8, 2022.

Zanchi Cesar Henrique et al: "A new approach in self-etching adhesive formulations: Replacing HEMA for surfactant dimethacrylate monomers", Journal of Biomedical Materials Research Part B: Applied Biomaterials, vol. 99B, No. 1, Jun. 28, 2011(Jun. 28, 2011), pp. 51-57, XP055949042, US ISSN: 1552-4973, DOI: 10.1002/jbm.b.31871 Retrieved from the Internet: URL:http://dx.doi.org/10.1002/jbm.b.31871.

Keiichi Hosaka et al: "Effect of wet vs. dry testing on the mechanical properties of hydrophilic self-etching primer polymers", European Journal of Oral Sciences, Munksgaard International Publishers, Copenhagen, DK, vol. 115, No. 3, Jun. 20, 2007 (Jun. 20, 2007), pp. 239-245, XP071780041, ISSN : 0909-8836, DOI: 10.1111/J.1600-0722.2007.00452.X.

Satoshi Inoue, Adhesive Systems from the Viewpoint of Adhesion Strategies, Journal of the Japanese Society of Dental Conservation, Oct. 2016, vol. 59, No. 6, p. 389-393.

* cited by examiner

*Primary Examiner* — Deve V Hall
(74) *Attorney, Agent, or Firm* — IPUSA, PLLC

(57) ABSTRACT

A two-agent type dental adhesive composition includes a first agent; and a second agent. The first agent includes a (meth)acrylate compound having an acid group, a (meth) acrylate compound having no acid group, water, and a water-soluble organic solvent. The second agent includes a multifunctional (meth)acrylate compound, a photopolymerization initiator, and a filler of 0 to 50 mass %. Both the first agent and the second agent substantially do not contain 2-hydroxyethyl methacrylate.

8 Claims, No Drawings

DENTAL ADHESIVE COMPOSITION

TECHNICAL FIELD

The present invention relates to a dental adhesive composition.

BACKGROUND ART

Two-agent type dental adhesive compositions are known to exhibit better adhesion to both tooth and to composite resin than one-agent type dental adhesive compositions. Such adhesion can be obtained by applying a first agent containing both an acidic compound and water to a target, acid-etching the target, removing water not involved in adhesion by air blowing, and then applying a second agent containing a polymerizable monomer and a photopolymerization initiator, followed by light irradiation.

As a two-agent type dental adhesive composition, for example, a dental adhesive system is disclosed that consists of a primer composition consisting of a polymerizable monomer having an acidic group, a polymerizable monomer having a hydroxyl group, and water, and a bonding composition consisting of an acylphosphine oxide-based photopolymerization initiator and a polymerizable monomer (see PTL 1).

CITATION LIST

Patent Literature

[PTL 1]
Japanese Laid-Open Patent Publication No. 2000-016911

SUMMARY OF INVENTION

Technical Problem

Conventional two-agent type dental adhesive compositions have a problem of decreasing strength over time in a wet environment.

It is an object of the present invention to provide a dental adhesive composition that does not decrease in strength over time in the wet environment.

Solution to Problem

According to one aspect of the present invention, a two-agent type dental adhesive composition includes: a first agent; and a second agent, wherein the first agent includes a (meth)acrylate compound having an acid group, a (meth) acrylate compound having no acid group, water, and a water-soluble organic solvent, wherein the second agent includes a multifunctional (meth)acrylate compound, a photopolymerization initiator, and a filler of 0 to 50 mass %, and wherein both the first agent and the second agent substantially do not contain 2-hydroxyethyl methacrylate.

Advantageous Effects of Invention

According to one aspect of the present invention, a dental adhesive composition that does not decrease in strength over time in a wet environment, can be provided.

DESCRIPTION OF EMBODIMENTS

Hereinafter, embodiments of the present invention will be described in detail.

<Dental Adhesive Composition>

A dental adhesive composition according to the present embodiment is a two-agent type dental adhesive composition including a first agent and a second agent.

<First Agent>

In the two-agent type dental adhesive composition, the first agent, also referred to as a pretreatment agent or a primer, includes a (meth)acrylate compound having an acid group, a (meth)acrylate compound having no acid group, water, and a water-soluble organic solvent, and substantially does not contain 2-hydroxyethyl methacrylate.

In the present specification, the term (meth)acrylate refers to at least one selected from acrylates or methacrylates.

<(Meth)Acrylate Compound Having Acid Group>

Examples of the (meth)acrylate compound having an acid group include, but are not limited to, (meth)acrylates having a phosphate group, (meth)acrylates having a pyrophosphate group, (meth)acrylates having a carboxyl group, (meth) acrylates having a thiophosphate group, (meth)acrylates having a sulfonate group, (meth)acrylates having a phosphonate group, and the like.

Examples of the (meth)acrylates having a phosphate group include 2-(meth)acryloyloxyethyl dihydrogen phosphate, bis[2-(meth)acryloyloxyethyl]hydrogen phosphate, 2-(meth)acryloyloxyethyl phenyl hydrogen phosphate, 6-(meth)acryloyloxyhexyl dihydrogen phosphate, 6-(meth) acryloyloxyhexyl phenyl hydrogen phosphate, 10-(meth) acryloyloxydecyl dihydrogen phosphate (hereinafter sometimes abbreviated as MDP), 1,3-di(meth)acryloyl propane-2-dihydrogen phosphate, 1,3-di(meth)acryloyl propane-2-phenyl hydrogen phosphate, bis[5-{2-(meth) acryloyloxyethoxycarbonyl} heptyl] hydrogen phosphate, and the like, and their acid chlorides, alkali metal salts, ammonium salts, and the like. Among these, 10-methacryloyloxydecyl dihydrogen phosphate (MDP) is preferred in terms of initial adhesion.

Examples of the (meth)acrylates having a pyrophosphate group include bis(2-(meth)acryloyloxyethyl) pyrophosphate, bis(4-(meth)acryloyloxybutyl) pyrophosphate, bis(6-(meth)acryloyloxyhexyl) pyrophosphate, bis(8-(meth)acryloyloxyoctyl) pyrophosphate, bis(10-(meth) acryloyloxydecyl) pyrophosphate, and the like, and their acid chlorides, alkali metal salts, ammonium salts, and the like.

Examples of the (meth)acrylates having a carboxyl group include 4-(meth)acryloyloxyethyl trimellitic acid (hereinafter sometimes abbreviated as 4-MET), 4-(meth)acryloyloxyethyl trimellitic anhydride (hereinafter sometimes abbreviated as 4-META), 4-(meth)acryloyloxydecyl trimellitic acid, 4-(meth)acryloyloxydecyl trimellitic anhydride, 11-(meth) acryloyloxy-1,1-undecanedicarboxylic acid, 1,4-di(meth) acryloyloxypyromellitic acid, 2-(meth)acryloyloxyethyl maleic acid, 2-(meth)acryloyloxyethyl phthalic acid, 2-(meth)acryloyloxyethyl hexahydrophthalic acid, and the like. Among these, 4-(meth)acryloyloxyethyl trimellitic anhydride (4-META) is preferred in terms of initial adhesion.

Examples of the (meth)acrylates having a thiophosphate group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate (hereinafter sometimes abbreviated as MDTP), 11-(meth)acryloyloxyundecyl dihydrogen thiophosphate, 12-(meth)acryloyloxydodecyl dihydrogen thiophosphate, 13-(meth)acryloyloxytridecyl dihydrogen thiophosphate, 14-(meth)acryloyloxytetradecyl dihydrogen thiophosphate, 15-(meth)acryloyloxypentadecyl dihydrogen thiophosphate, 16-(meth)acryloyloxyhexadecyl dihydrogen thiophosphate, 17-(meth)acryloyloxyheptadecyl dihydrogen thiophosphate, 18-(meth)acryloyloxyoctadecyl dihydrogen thiophosphate, 19-(meth)acryloyloxynonadecyl dihydrogen thiophosphate, 20-(meth)acryloyloxyicosyl dihydrogen thiophosphate, and the like, and their acid chlorides, alkali metal salts, ammonium salts, and the like. Among these, 10-(meth)acryloyloxydecyl dihydrogen thiophosphate (MDTP) is preferred in terms of initial adhesion.

Examples of the (meth)acrylates having a sulfonate group include 2-(meth)acrylamide-2 methylpropane sulfonic acid, styrene sulfonic acid, 2-sulfoethyl (meth)acrylate, and the like.

Examples of the (meth)acrylates having a phosphonate group include 2-(meth)acryloyloxyethyl phenyl phosphonate, 5-(meth)acryloyloxypentyl-3 phosphonopropionate, 6-(meth)acryloyloxyhexyl-3 phosphonopropionate, 10-(meth)acryloyloxydecyl-3 phosphonopropionate, 6-(meth)acryloyloxyhexyl-3 phosphonoacetate, 10-(meth)acryloyloxydecyl-3 phosphonoacetate, and the like, and their acid chlorides, alkali metal salts, ammonium salts, and the like.

The (meth)acrylate compound having the acid group may be used alone or in combination of two or more.

The content of the (meth)acrylate compound having the acid group in the first agent is not particularly limited, but is, for example, 5 to 30 mass %, and preferably 10 to 20 mass %, for 100 mass % of the first agent. When the content of the (meth)acrylate compound having the acid group in the first agent is 5 to 30 mass %, the initial adhesion of the dental adhesive composition is improved.

<(Meth)Acrylate Compound Having No Acid Group>

The (meth)acrylate compound having no acid group is not particularly limited, but is, for example, di(meth)acrylate compound. The di(meth)acrylate compound is preferably di(meth)acrylate compounds having a molecular weight of less than 400, such as 2-hydroxy-1,3-dimethacryloyloxy propane, diethylene glycol dimethacrylate, triethylene glycol dimethacrylate, polyethylene glycol #200 dimethacrylate, 1,6-hexanediol dimethacrylate, 1,9-nonanediol dimethacrylate, 1,10-decanediol dimethacrylate, neopentyl glycol dimethacrylate, and the like, for example. The (meth)acrylate compound having no acid group may be used alone or in combination of two or more.

The content of the (meth)acrylate compound having no acid group in the first agent is not particularly limited, but is, for example, 1 to 40 mass %, and preferably 5 to 25 mass %, for 100 mass % of the first agent. When the content of the (meth)acrylate compound having no acid group in the first agent is 1 to 40 mass %, the adhesion of the dental adhesive composition is improved, and the mechanical strength of the hardened body of the dental adhesive composition is improved.

<Water>

As water, ion-exchanged water or distilled water is preferably used, although not particularly limited. When the first agent contains water, because the acid group of the (meth)acrylate having the acid group is dissociated, the solubility of the smear layer on the tooth surface is increased, and the tooth demineralization and the permeability into tooth of the dental adhesive composition as a primer, are improved. Therefore, when the tooth surface is pretreated with the first agent, the permeability into tooth of the dental adhesive composition as a primer is improved, and the adhesion of the dental adhesive composition is improved.

The content of water in the dental composition is not particularly limited, but is, for example, preferably 1 to 50 mass %, and more preferably 5 to 40 mass %, for 100 mass % of the first agent. When the content of water in the dental composition is 1 to 50 mass %, the solubility of the smear layer on the tooth surface is increased, and the tooth demineralization and the permeability into tooth of the dental adhesive composition as a primer, are improved.

<Water-Soluble Organic Solvent>

Examples of the water-soluble organic solvent include, but are not limited to, methanol, ethanol, propanol, isopropanol, butanol, pentanol, acetone, methyl ethyl ketone, methyl isobutyl ketone, toluene, xylene, ethyl acetate, butyl acetate, cellosolve, tetrahydrofuran, dioxane, dichloromethane, chloroform, carbon tetrachloride, trichloroethylene, dimethylformamide, dimethyl sulfoxide, and the like. The water-soluble organic solvent may be used alone or in combination of two or more. Among these, ethanol, acetone, isopropanol, and butanol are preferred.

The content of the water-soluble organic solvent in the first agent is not particularly limited, but is, for example, 10 to 50 mass %, and preferably 20 to 40 mass %, for 100 mass % of the first agent. When the content of the water-soluble organic solvent in the dental adhesive composition is 10 mass % or more, the uniformity of the dental composition is improved, and when 50 mass % or less, the adhesion of the dental adhesive composition as a primer is improved.

<Other Component>

The first agent may further contain a photopolymerization initiator, a tertiary amine, a polymerization inhibitor, and a filler.

Examples of the photopolymerization initiator include, but are not particularly limited to, α-diketone compounds such as camphorquinone; acylphosphine oxide compounds such as 2,4,6-trimethylbenzoyldiphenylphosphine oxide, 2,4,6-trimethoxybenzoyldiphenylphosphine oxide, 2,6-dimethylbenzoyldiphenylphosphine oxide, 2,6-dimethoxybenzoyldiphenylphosphine oxide; benzyl ketal, diacetyl ketal, benzyl dimethyl ketal, benzyl diethyl ketal, benzyl bis(2-methoxyethyl) ketal, 4,4'-dimethyl(benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl) ketone, 4,4'-bis(diethylamino) benzophenone, and compounds containing an azide group. The photopolymerization initiator may be used alone or in combination of two or more.

The content of the photopolymerization initiator in the first agent is not particularly limited, but is, for example, 0.01 to 5 mass %, and preferably 2 to 4 mass %, for 100 mass % of the first agent. When the content of the photopolymerization initiator in the first agent is 0.01 to 5 mass %, the adhesion of the dental adhesive composition is improved, and the storage stability of the dental adhesive composition as a primer is improved.

The tertiary amine may function as a polymerization accelerator. The tertiary amine is not particularly limited, but is preferably an aromatic tertiary amine such as ethyl 4-dimethylaminobenzoate, and the like, for example. When the tertiary amine is contained, the content of the tertiary amine in the first agent is not particularly limited, but is, for example, 0.01 to 3 mass %, and preferably 0.1 to 1 mass %, for 100 mass % of the first agent.

The polymerization inhibitor is not particularly limited, but is dibutylhydroxytoluene, 2,6-t-butyl-2,4-xylenol, and the like, for example. When the polymerization inhibitor is included, the content of the polymerization inhibitor in the first agent is not particularly limited, but is, for example, 0.01 to 3 mass %, and preferably 0.1 to 1 mass %, for 100 mass % of the first agent.

The filler is not particularly limited, but is preferably an inorganic filler, such as colloidal silica, fine particle silica whose surface is hydrophobized, aluminum oxide, and the like. When the filler is contained, the content of the filler in the first agent is not particularly limited, but is, for example, 0.01 to 30 mass %, and is preferably 0.1 to 10 mass %, for 100 mass % of the first agent.

<Excluded Component in First Agent>

The first agent substantially does not contain 2-hydroxyethyl methacrylate (hereinafter sometimes abbreviated as HEMA). As used herein, "substantially does not contain" means that the target ingredient, such as HEMA, is not intentionally included. The target ingredient that is "substantially does not contained" may be included as an unavoidable impurity. The content of the target ingredient as the unavoidable impurity is preferably less than 1%.

When the first agent substantially contains 2-hydroxyethyl methacrylate (HEMA), the strength of the hardened layer of the dental adhesive composition decreases over time due to water absorption. In contrast, in the present embodiment, when the first agent substantially does not contain 2-hydroxyethyl methacrylate (HEMA), a decrease in strength over time of the hardened layer of the dental adhesive composition due to water absorption can be minimized.

For the same reason as 2-hydroxyethyl methacrylate (HEMA), it is preferable that the first agent substantially does not contain a monofunctional (meth)acrylate compound having a hydroxyl group, such as 2,3-dihydroxypropyl methacrylate, and a monofunctional (meth)acrylamide, such as N,N-diethylacrylamide.

The first agent preferably has a pH of 1.2 to 2.0, more preferably 1.5 to 2.0. When the pH of the first agent is set to 1.2 to 2.0, the solubility of the smear layer on the tooth surface and the tooth demineralization are improved, and the adhesion of the dental adhesive composition is improved.

<Second Agent>

In the two-agent type dental adhesive composition, the second agent, also referred to as a bonding agent (or bond), includes a multifunctional (meth)acrylate compound, a photopolymerization initiator, and a filler of 0 to 50 mass %, and substantially does not contain 2-hydroxyethyl methacrylate (HEMA).

<Multifunctional (Meth)acrylate Compound>

The multifunctional (meth)acrylate compound in the second agent is not particularly limited, but is preferably a di(meth)acrylate compound, more preferably containing both a di(meth)acrylate compound having a molecular weight of 400 or more and a di(meth)acrylate compound having a molecular weight of less than 400.

Examples of the di(meth)acrylate compound having a molecular weight of 400 or more include aliphatic di(meth) acrylate compounds having a molecular weight of 400 or more and aromatic di(meth)acrylate compounds having a molecular weight of 400 or more.

Specific examples of the aliphatic di(meth)acrylate compounds having a molecular weight of 400 or more include 1,6-bis-[2-methacryloyloxyethoxycarbonylamino]-2,4,4-trimethylhexane (UDMA), polyethylene glycol #400 dimethacrylate, polyethylene glycol #600 dimethacrylate, polyethylene glycol #1000 dimethacrylate, and the like, for example.

Specific examples of the aromatic di(meth)acrylate compounds having a molecular weight of 400 or more include bisphenol A diglycidyl methacrylate (Bis-GMA), 2-(4-(meth)acryloyloxydiethoxyphenyl)-2-(4-(meth)acryloyloxytriethoxyphenyl) propane, 2-(4-(meth)acryloyloxydipropoxyphenyl)-2-(4-(meth)acryloyloxytriethoxyphenyl) propane, 2,2-bis(4-(meth)acryloyloxypropoxyphenyl) propane, 2,2-bis(4-(meth)acryloyloxyisopropoxyphenyl) propane, and the like.

The di(meth)acrylate compound having a molecular weight of less than 400 is not particularly limited, but is preferably a di(meth)acrylate compound having a molecular weight of less than 300.

Examples of the di(meth)acrylate compound having a molecular weight of less than 300 include 2-hydroxy-1,3-dimethacryloyloxypropane, diethylene glycol dimethacrylate, triethylene glycol dimethacrylate, polyethylene glycol #200 dimethacrylate, 1,6-hexanediol dimethacrylate, 1,9-nonanediol dimethacrylate, 1,10-decanediol dimethacrylate, neopentyl glycol dimethacrylate, and the like. Among these, di(meth)acrylate compounds containing a hydroxyl group are preferred, and 2-hydroxy-1,3-dimethacryloyloxypropane is more preferred.

The content of the multifunctional (meth)acrylate compound in the second agent is not particularly limited, but is, for example, 50 to 99 mass %, and preferably 60 to 95 mass %, for 100 mass % of the second agent. When the content of the multifunctional (meth)acrylate compound in the second agent is 50 to 99 mass %, the adhesion of the dental adhesive composition is improved, and the mechanical strength of the hardened body of the dental adhesive composition is improved.

The proportion of the content of the di(meth)acrylate compound having a molecular weight of less than 400 to the content of the di(meth)acrylate compound having a molecular weight of 400 or more in the second agent is freely-determined, but is preferably 0.5 to 2, and even more preferably 0.8 to 1.4. When the proportion of the content of the di(meth)acrylate compound having a molecular weight of less than 400 to the content of the di(meth)acrylate compound having a molecular weight of 400 or more in the second agent is 0.5 to 2, adhesion of the dental adhesive composition is improved.

<Photopolymerization Initiator>

Examples of the photopolymerization initiator in the second agent include, but are not particularly limited to, α-diketone compounds such as camphorquinone; acylphosphine oxide compounds such as 2,4,6-trimethylbenzoyldiphenylphosphine oxide, 2,4,6-trimethoxybenzoyldiphenylphosphine oxide, 2,6-dimethylbenzoyldiphenylphosphine oxide, 2,6-dimethoxybenzoyldiphenylphosphine oxide; benzyl ketal, diacetyl ketal, benzyl dimethyl ketal, benzyl diethyl ketal, benzyl bis(2-methoxyethyl) ketal, 4,4'-dimethyl(benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl) ketone, 4,4'-bis(diethylamino) benzophenone, and compounds containing an azide group. The photopolymerization initiator may be used alone or in combination of two or more.

The content of the photopolymerization initiator in the second agent is not particularly limited, but is, for example, 0.01 to 8 mass %, and preferably 3 to 6 mass %, for 100 mass % of the second agent. When the content of the photopolymerization initiator in the second agent is 0.01 to 8 mass %, the adhesion of the dental adhesive composition is improved, and the storage stability of the dental adhesive composition as a bonding agent is improved.

<Filler>

The second agent may include the filler. The content of the filler in the second agent is 0 to 50 mass %, and preferably 0.1 to 20 mass %. That is, when the second agent includes the filler, the filler of more than 50 mass % is not contained.

When the content of the filler in the second agent exceeds 50 mass %, the operability may be impaired and the adhesion may be reduced because the polymerized component is reduced. In contrast, when the content of the filler in the second agent is 50 mass % or less, the dispersibility of the second agent is improved and the storage stability of the dental adhesive composition as a bonding agent is improved.

<Other Ingredient>

The second agent may further include a tertiary amine, and a polymerization inhibitor.

The tertiary amine in the second agent may function as a polymerization accelerator, as in the first agent. The tertiary amine in the second agent is not particularly limited, but is preferably an aromatic tertiary amine such as ethyl 4-dimethylaminobenzoate, and the like, for example. When the tertiary amine is contained, the content of the tertiary amine in the second agent is not particularly limited, but is, for example, 0.01 to 5 mass %, and preferably 1 to 4 mass %, for 100 mass % of the second agent.

The polymerization inhibitor in the second agent is not particularly limited but is dibutylhydroxytoluene, 2,6-t-butyl-2,4-xylenol, and the like, for example. When the polymerization inhibitor is included, the content of the polymerization inhibitor in the second agent is not particularly limited, but is, for example, 0.01 to 3 mass %, and preferably 0.1 to 1 mass %, for 100 mass % of the second agent.

<Excluded Component in Second Agent>

The second agent substantially does not contain 2-hydroxyethyl methacrylate (HEMA). When the second agent substantially contains HEMA, the strength of the hardened layer of the dental adhesive composition decreases over time due to water absorption. In contrast, in the present embodiment, when the second agent substantially does not contain HEMA, a decrease in strength over time of the hardened layer of the dental adhesive composition due to water absorption can be minimized.

For the same reason as 2-hydroxyethyl methacrylate (HEMA), it is preferable that the second agent substantially does not contain a monofunctional (meth)acrylate compound having a hydroxyl group, such as 2,3-dihydroxypropyl methacrylate, and a monofunctional (meth)acrylamide, such as N,N-diethylacrylamide.

It is preferable that the second agent substantially does not contain the (meth)acrylate compound having an acid group. When the second agent substantially contains the (meth)acrylate compound having an acid group, some types of photopolymerization initiators may cause degradation, resulting in a decrease in polymerizability. In contrast, when the second agent substantially does not contain the (meth)acrylate compound having an acid group, the storage stability of the photopolymerization initiator in the second agent can be improved and the decrease in polymerizability in the dental adhesive composition can be minimized.

It is even more preferable that the second agent substantially does not contain a chemical polymerization initiator. When the second agent contains the chemical polymerization initiator, the storage stability of the second agent as a bonding agent may decrease. Examples of such chemical polymerization initiators include vanadium compounds such as vanadium acetylacetonate.

Because both the first agent and the second agent of the dental adhesive composition according to the present embodiment substantially do not contain 2-hydroxyethyl methacrylate (HEMA) as described above, the composition is resistant to strength degradation over time in a wet environment. Therefore, according to the present embodiment, the dental adhesive composition that improves adhesion and improves the mechanical strength of the hardened body can be obtained.

<Mode of Use of Dental Composition>

The dental adhesive composition according to the present embodiment is used by applying the first agent described above to a target, followed by air blowing, and then applying the second agent described above to the target. Here, the target may be either tooth or restorations (composite resin prostheses and the like). The air blowing may be performed by a publicly-known method and may be performed immediately after application of the first agent.

The manner in which the first agent is applied to the target is freely-determined, but for example, the first agent may be applied to the target by a publicly-known method. The manner in which the second agent is applied to the target is freely-determined, but for example, the second agent may be applied to the target to which the first agent is applied by a publicly-known method.

The dental adhesive composition according to the present embodiment can be used in the same manner as the conventional two-agent type dental adhesive composition by being used in such a manner, and is therefore easy to handle as a two-agent type dental adhesive composition.

<Application of Dental Adhesive Composition>

The application of the dental adhesive composition according to the present embodiment is not particularly limited but may include various dental materials. Examples of the application of the dental adhesive composition according to the present embodiment include dental cement, dental adhesive, dental temporary sealing material, dental coating material, dental hard resin, dental cutting resin material, dental temporary restorative material, dental filler, dentifrice, and the like. Among these, the dental adhesive composition of the present embodiment is suitably used for dental adhesive.

EXAMPLE

Hereinafter, the present invention will be further described using Examples and Comparative Examples. In the following, "part" and "%" are based on mass unless otherwise specified. In addition, various tests and evaluations are performed according to the following methods.

<Test Sample (First Agent)>

A first agent, which constitutes a two-agent type dental adhesive composition, was prepared with the formulation presented in Table 1. The first agent, which was formulated in Table 1, had a pH of 1.5.

TABLE 1

| PRIMER FORMULATION | [wt %] |
|---|---|
| ACETONE | 25 |
| GDMA | 15 |
| TEGDMA | 5 |
| AEROSIL R972 | 5 |
| 4-META | 10 |
| MDP | 10 |
| DISTILLED WATER | 25 |
| CQ | 1 |
| EPA | 1 |
| TPO | 2 |
| BHT | 1 |
| TOTAL | 100 |

The specifications of ingredients indicated by abbreviations or product names in Table 1 are as follows.

GDMA: 2-hydroxy-1,3-dimethacryloyloxypropane
TEGDMA: triethylene glycol dimethacrylate
AEROSIL (registered trademark) R972: fine particle silica surface-treated with dimethyldichlorosilane (DDS) (manufactured by Nippon Aerosil Co., Ltd.)
4-META: 4-methacryloyloxyethyl trimellitic anhydride
MDP: 10-methacryloyloxydecyl dihydrogen phosphate
CQ: camphorquinone
EPA: ethyl 4-dimethylaminobenzoate
TPO: 2,4,6-trimethoxybenzoyldiphenylphosphine oxide
BHT: dibutylhydroxytoluene <Test Sample (Second Agent)>

A second agent, which constitutes the two-agent type dental adhesive composition, was prepared with the formulation presented in Table 2.

TABLE 2

| BONDING AGENT FORMULATION [wt %] | EXAMPLE 1 | EXAMPLE 2 | EXAMPLE 3 | EXAMPLE 4 | EXAMPLE 5 |
|---|---|---|---|---|---|
| Bis-GMA | 13 | | 13 | 13 | 13 |
| BPE-200 | | 13 | | | |
| UDMA | 30 | 30 | 30 | 30 | 30 |
| GDMA | 45 | 45 | | | 45 |
| TEGDMA | | | 45 | | |
| NPG | | | | 45 | |
| HEMA | | | | | |
| MDP | | | | | |
| CQ | 2 | 2 | 2 | 2 | 2 |
| EPA | 2 | 2 | 2 | 2 | 2 |
| TPO | 2 | 2 | 2 | 2 | 2 |
| BHT | 1 | 1 | 1 | 1 | 1 |
| AEROSIL RX50 | 5 | 5 | 5 | 5 | |
| AEROSIL R812 | | | | | 5 |
| AEROSIL RX200 | | | | | |
| TOTAL | 100 | 100 | 100 | 100 | 100 |

| BONDING AGENT FORMULATION [wt %] | EXAMPLE 6 | EXAMPLE 7 | COMPARATIVE EXAMPLE 1 | COMPARATIVE EXAMPLE 2 | COMPARATIVE EXAMPLE 3 |
|---|---|---|---|---|---|
| Bis-GMA | 13 | 18 | 13 | 13 | 13 |
| BPE-200 | | | | | |
| UDMA | 30 | 30 | 30 | 30 | 30 |
| GDMA | 45 | | 30 | 15 | 15 |
| TEGDMA | | 45 | | | |
| NPG | | | | | |
| HEMA | | | 15 | 30 | 15 |
| MDP | | | | | 15 |
| CQ | 2 | 2 | 2 | 2 | 2 |
| EPA | 2 | 2 | 2 | 2 | 2 |
| TPO | 2 | 2 | 2 | 2 | 2 |
| BHT | 1 | 1 | 1 | 1 | 1 |
| AEROSIL RX50 | | | 5 | 5 | 5 |
| AEROSIL R812 | | | | | |
| AEROSIL RX200 | 5 | | | | |
| TOTAL | 100 | 100 | 100 | 100 | 100 |

The specifications of ingredients indicated by abbreviations or product names in Table 2 are as follows.

Bis-GMA: bisphenol A diglycidyl methacrylate

BPE-200: ethoxylated bisphenol A dimethacrylate

UDMA: 1,6-bis-[2-methacryloyloxyethoxycarbonylamino]-2,4,4-trimethylhexane

GDMA: 2-hydroxy-1,3-dimethacryloyloxypropane

TEGDMA: triethylene glycol dimethacrylate

NPG: neopentyl glycol dimethacrylate

HEMA: 2-hydroxyethyl methacrylate

MDP: 10-methacryloyloxydecyl dihydrogen phosphate

CQ: camphorquinone

EPA: ethyl 4-dimethylaminobenzoate

TPO: 2,4,6-trimethoxybenzoyldiphenylphosphine oxide

BHT: dibutylhydroxytoluene

AEROSIL (registered trademark) RX50: fine particle silica surface-treated with hexamethyldisilazane (manufactured by Nippon Aerosil Co., Ltd.)

AEROSIL (registered trademark) R812: fine particle silica surface-treated with hexamethyldisilazane (manufactured by Nippon Aerosil Co., Ltd.)

AEROSIL (registered trademark) RX200: fine particle silica surface-treated with hexamethyldisilazane (manufactured by Nippon Aerosil Co., Ltd.)

35 MPa; and poor: less than 25 MPa, and for dentin on the following criteria: excellent: 45 MPa or more; good: 35 MPa or more and less than 45 MPa; and poor: less than 35 MPa. The results are presented in Table 3.

<Polymerization Rate>

A ring of 10 mm in diameter and 1.0 mm thick, made of a OHP sheet, was placed on a glass slide, and the ring was overfilled with the second agent while ensuring that no air bubbles were formed. An OHP sheet was then placed thereon, and pressure welded using glass slides. Using the light irradiator (G-Light Prima II Plus, manufactured by GC Corporation), light irradiation at one point in the center was applied on the back and front surfaces for 10 seconds each to harden the bond. Five minutes after preparation, for the hardened body obtained, the peak after polymerization was measured using the ATR method of FT-IR (NICOLET (registered trademark) iS50, manufactured by Thermo Fisher Scientific Inc.). Similarly, the bond before hardening was measured by FT-IR and the peak before polymerization was measured. The peaks before and after polymerization were compared, and the polymerization rate was calculated from the following equation. All measurements were performed by setting N=5. The polymerization rate was evaluated based on the following criteria: excellent: 75% or more; good: 60% or more and less than 75%; and poor: less than 60%. The results are presented in Table 3.

[Equation 1]

$$\text{POLYMERIZATION RATE} = 1 - \frac{\dfrac{\text{AFTER POLYMERIZATION } C=C(1640\ \text{cm}^{-1})}{\text{AFTER POLYMERIZATION}(1610\ \text{cm}^{-1})}}{\dfrac{\text{BEFORE POLYMERIZATION } C=C(1640\ \text{cm}^{-1})}{\text{BEFORE POLYMERIZATION}(1610\ \text{cm}^{-1})}}$$

<Shear Adhesion Strength>

The shear adhesion strength was measured with reference to the adhesion test according to ISO 29022 (2013). Bovine mandibular anterior teeth were embedded with room temperature polymerized resin. Then, enamel and dentin were exposed using #120 SiC water-resistant abrasive paper, and the test surface was polished using #400 SiC water-resistant abrasive paper. A self-etching primer (the first agent or a first fluid) was applied to the test surface using an applicator and allowed to stand for 10 seconds. A bond (the second agent or a second fluid) was then applied using an applicator. After the bond was equalized with low-pressure air, a plastic mold with a hole of 2.38 mm in diameter was placed on the test surface, and the mold was irradiated with light using a light irradiator (G-Light Prima II Plus, manufactured by GC Corporation) for 10 seconds to harden the bond. The hole was filled with a composite resin (Clearfil AP-X, manufactured by Kuraray Noritake Dental Inc.) and irradiated with light using the light irradiator for 20 seconds. The mold was removed so that no load was applied to the specimen, and the specimen was stored in water at 37 °C for 24 hours. After measuring the dimensions of the obtained specimen, a shear adhesion test was performed using a universal testing machine (EZ-S, manufactured by Shimadzu Corporation) (crosshead speed: 1 mm/min), and the shear adhesion strength was calculated from the dimensions and the stress values obtained in the shear adhesion test. The measurement was performed by setting N=5. The shear adhesion strength was evaluated for enamel on the following criteria: excellent: 35 MPa or more; good: 25 MPa or more and less than <Bending Strength>

The bending strength was measured by the bending test according to ISO 4049 (2019). A glass plate and a mold made of an OHP sheet for measuring dimensions were placed on a metal plate, and the mold was filled with the bond (the second fluid). Pressure bonding was performed using OHP sheets and glass plates. From the outside of the glass plates, light irradiation at nine points was applied to the back and front surfaces of the glass plate for 10 seconds each using the light irradiator (G-Light Prima II Plus, manufactured by GC Corporation) to harden the bonds. After standing in a thermostatic chamber at 37 °C for 15 minutes, the specimen was removed from the mold, deburred using #320 water-resistant abrasive paper, and stored in water at 37 °C for 24 hours or for 1 week. After measuring the dimensions of the obtained specimen, a three-point bending test was performed using a universal testing machine (AG-IS, manufactured by Shimadzu Corporation) (crosshead speed: 1 mm/min). From the dimensions and the stress values obtained in the three-point bending test, the three-point bending strength was calculated and the bending strength after 1 day (24 hours) and after 1 week was measured. All measurements were performed by setting N=5. The bending strength was evaluated on the following criteria: excellent: 120 MPa or more; good: 100 MPa or more and less than 120 MPa; and poor: less than 100 MPa. The results are presented in Table 3.

<Decrease Rate of Bending Strength>

The decrease rate of bending strength was calculated from the following equation from the bending strength after one day and after one week obtained by the above bending test. When the decrease rate of bending strength is negative, it indicates an increase in bending strength. This is because the water absorption of the hardened dental adhesive composition was suppressed, and furthermore, the decrease in polymerizability was reduced, and the polymerization progressed over time. The results are presented in Table 3.

$$\text{DECREASE RATE OF BENDING STRENGTH (\%)} = \frac{\text{BENDING STRENGTH AFTER ONE DAY} - \text{BENDING STRENGTH AFTER ONE WEEK}}{\text{BENDING STRENGTH AFTER ONE DAY}} \times 100 \quad \text{[Equation 2]}$$

<Vickers Hardness>

The Vickers hardness was measured by a Vickers hardness test. A ring of 15 mm in diameter and 1.5 mm thick, made of a OHP sheet, was placed on a glass slide, and the ring was overfilled with the bond (the second fluid) while ensuring that no air bubbles were formed. An OHP sheet was then placed thereon, and pressure welded using glass slides. Using the light irradiator (G-Light Prima II Plus, manufactured by GC Corporation), light irradiation at one point in the center and eight points on the circumference was applied on the back and front surfaces for 10 seconds each to harden the bond. The obtained hardened body was polished sequentially using #1200, #2400, and #4000 SiC water-resistant abrasive paper, and stored in water at 37 °C for 24 hours or for 1 week. The Vickers hardness of the obtained specimen after 1 day (24 hours) and after 1 week was measured using a micro-Vickers tester (HMV-G21D1, manufactured by Shimadzu Corporation) (HV 0.2, retention time 10 seconds, 3 specimens, N=5 per specimen). The Vickers hardness was evaluated on the following criteria: excellent: 25 HV or more; good: 20 HV or more and less than 25 HV; and poor: less than 20 HV. The results are presented in Table 3.

<Decrease Rate in Vickers Hardness>

The decrease rate in Vickers hardness was calculated from the Vickers hardness after one day and after one week obtained by the above Vickers hardness test, using the following equation. The results are presented in Table 3.

$$\text{DECREASE RATE } O \text{ VICKERS HARDNESS (\%)} = \frac{\text{VICKERS HARDNESS AFTER ONE DAY} - \text{VICKERS HARDNESS AFTER ONE WEEK}}{\text{VICKERS HARDNESS AFTER ONE DAY}} \times 100 \quad \text{[Equation 3]}$$

<Water Absorption Amount>

The water absorption amount was measured by a water absorption test according to ISO 4049 (2019). A ring of 15 mm in diameter and 1.0 mm thick, made of a OHP sheet, was placed on a glass slide, and the ring was overfilled with the bond (the second fluid) while ensuring that no air bubbles were formed. An OHP sheet was then placed thereon, and pressure welded using glass slides. Using the light irradiator (G-Light Prima II Plus, manufactured by GC Corporation), light irradiation at one point in the center and eight points on the circumference was applied on the back and front surfaces for 20 seconds each to harden the bond. The obtained hardened body was stored as a test specimen in a desiccator in a thermostat set at 37 °C. The volume (V) and weight (m1) of the constant-volume specimen were repeatedly determined until the mass loss was less than or equal to 0.1 g per 24 hours. The specimen was immersed in distilled water in a sample container and left in the thermostat set at 37 °C for 1 week, after which the weight (m2) of the weighed specimen was determined. The water absorption amount was calculated from the following equation. The measurement was performed by setting N=5. The water absorption amount was evaluated the following criteria: excellent: less than 50 μg/mm$^3$; good: 50 μg/mm$^3$ or more and less than 60 μg/mm$^3$; and poor: 60 μg/mm$^3$ or more. The results are presented in Table 3.

$$\text{WATER ABSORPTION AMOUNT} = \frac{m2 - m1}{V} \quad \text{[Equation 4]}$$

TABLE 3

| EVALUATION | | EXAMPLE 1 | EXAMPLE 2 | EXAMPLE 3 | EXAMPLE 4 | EXAMPLE 5 | EXAMPLE 6 |
|---|---|---|---|---|---|---|---|
| ADHESIVE STRENGTH TO SHEAR [MPa] | ENAMEL | 39.9 | 40.1 | 37.7 | 39.1 | 37.4 | 40.3 |
| | DENTIN | 48.2 | 46.6 | 49.1 | 47.2 | 46.9 | 49.2 |
| POLYMERIZATION RATE [%] | | 75.8 | 75.4 | 77.7 | 79.2 | 77.1 | 75 |
| BENDING STRENGTH (AFTER ONE DAY) [MPa] | | 129 | 118.8 | 125.1 | 116.9 | 128 | 130 |
| BENDING STRENGTH (AFTER ONE WEEK) [MPa] | | 126.1 | 123.6 | 124.9 | 118.8 | 124.4 | 129.3 |
| DECREASE RATE OF BENDING STRENGTH [%] | | 2.2 | −4.0 | 0.2 | −1.6 | 2.8 | 0.5 |
| VICKERS HARDNESS (AFTER ONE DAY) [HV] | | 26.3 | 24.9 | 27.2 | 28.2 | 27 | 26.7 |
| VICKERS HARDNESS (AFTER ONE WEEK) [HV] | | 25.5 | 24.4 | 26.6 | 27.1 | 26.1 | 26.3 |

TABLE 3-continued

| | | | | | | |
|---|---|---|---|---|---|---|
| DECREASE RATE OF VICKERS HARDNESS [%] | 3.0 | 2.0 | 3.7 | 3.9 | 3.3 | 1.5 |
| WATER ABSORPTION AMOUNT [μg/mm$^3$] | 41 | 41.3 | 32.2 | 23.8 | 39.8 | 37 |

| EVALUATION | | EXAMPLE 7 | COMPARATIVE EXAMPLE 1 | COMPARATIVE EXAMPLE 2 | COMPARATIVE EXAMPLE 3 |
|---|---|---|---|---|---|
| ADHESIVE STRENGTH TO SHEAR [MPa] | ENAMEL | 36.5 | 34.5 | 30.2 | 32.4 |
| | DENTIN | 48 | 44.9 | 39.6 | 41.4 |
| POLYMERIZATION RATE [%] | | 76.1 | 84 | 85.9 | 73.4 |
| BENDING STRENGTH (AFTER ONE DAY) [MPa] | | 123.7 | 126.5 | 124.8 | 121.3 |
| BENDING STRENGTH (AFTER ONE WEEK) [MPa] | | 121.6 | 120.4 | 108.3 | 109.3 |
| DECREASE RATE OF BENDING STRENGTH [%] | | 1.7 | 4.8 | 13.2 | 9.9 |
| VICKERS HARDNESS (AFTER ONE DAY) [HV] | | 28.5 | 23.2 | 17.7 | 18.4 |
| VICKERS HARDNESS (AFTER ONE WEEK) [HV] | | 27.8 | 21.4 | 15.1 | 16.5 |
| DECREASE RATE OF VICKERS HARDNESS [%] | | 3.1 | 7.8 | 14.7 | 10.3 |
| WATER ABSORPTION AMOUNT [μg/mm$^3$] | | 33.5 | 62.8 | 78.7 | 68.3 |

From Table 1 to 3, it can be seen that when the second agents of Examples 1 to 7 are used, all items are excellent or good, indicating that the adhesive compositions exhibit good adhesion and are resistant to strength degradation over time in a wet environment.

In contrast, when HEMA is blended (Comparative Examples 1, 2) and when HEMA and MDP are blended (Comparative Example 3) in the second agent, it can be seen that the bending strength and the Vickers hardness decrease after 1 week of immersion in water.

Although the embodiments of the present invention have been described above, the present invention is not limited to specific embodiments, and various modifications and changes are possible within the scope of the invention described in the claims.

The present application claims priority to Japanese Patent Application No. 2021-17790, filed Feb. 5, 2021, with the Japanese Patent Office, the contents of which are incorporated herein by reference in their entirety.

The invention claimed is:

1. A two-agent dental adhesive composition comprising:

a first agent; and a second agent, wherein the first agent includes a (meth)acrylate compound having an acid group, a (meth)acrylate compound having no acid group, water of 5 to 40 mass % for 100 mass % of the first agent, and a water-soluble organic solvent of 20 to 40 mass % for 100 mass % of the first agent, wherein the second agent includes a multifunctional (meth)acrylate compound, a photopolymerization initiator, and a filler of 0 to 50 mass % for 100 mass % of the second agent, and wherein both the first agent and the second agent substantially do not contain 2-hydroxyethyl methacrylate.

2. The dental adhesive composition according to claim 1, wherein the multifunctional (meth)acrylate compound in the second agent contains a di(meth)acrylate compound having a molecular weight of 400 or more and a di(meth)acrylate compound having a molecular weight of less than 400.

3. The dental adhesive composition according to claim 2, wherein a proportion of a content of the di(meth)acrylate compound having the molecular weight of less than 400 to a content of the di(meth)acrylate compound having the molecular weight of 400 or more in the second agent is 0.5 to 2.

4. The dental adhesive composition according to claim 2, wherein the di(meth)acrylate compound having the molecular weight of 400 or more in the second agent includes an aromatic di(meth)acrylate compound and an aliphatic di(meth)acrylate compound.

5. The dental adhesive composition according to claim 2, wherein the di(meth)acrylate compound having the molecular weight of less than 400 in the second agent is a di(meth) acrylate compound containing a hydroxyl group.

6. The dental adhesive composition according to claim 1, wherein the second agent substantially does not contain the (meth)acrylate compound having the acid group.

7. The dental adhesive composition according to claim 1, wherein a pH of the first agent is 1.2 to 2.0.

8. The dental adhesive composition according to claim 1, wherein the dental adhesive composition is used by applying the first agent to a target, followed by air blowing, and then applying the second agent to the target.

* * * * *